US012082955B2

(12) United States Patent
Feuerlein et al.

(10) Patent No.: US 12,082,955 B2
(45) Date of Patent: Sep. 10, 2024

(54) METHOD FOR ACTUATING A MEDICAL IMAGING DEVICE AND MEDICAL IMAGING DEVICE

(71) Applicant: Siemens Healthcare GmbH, Erlangen (DE)

(72) Inventors: Ute Feuerlein, Erlangen (DE); Thomas Allmendinger, Forchheim (DE); Matthias Baer-Beck, Spardorf (DE); Thomas Flohr, Uehlfeld (DE); Ulrich Foerner, Ebensfeld (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 279 days.

(21) Appl. No.: 17/553,899

(22) Filed: Dec. 17, 2021

(65) Prior Publication Data

US 2022/0192612 A1 Jun. 23, 2022

(30) Foreign Application Priority Data

Dec. 22, 2020 (DE) ...................... 10 2020 216 524.6

(51) Int. Cl.
*A61B 6/10* (2006.01)
*A61B 6/00* (2006.01)
(Continued)

(52) U.S. Cl.
CPC ............... *A61B 6/12* (2013.01); *A61B 6/032* (2013.01); *A61B 6/4429* (2013.01); *A61B 6/461* (2013.01); *A61B 6/54* (2013.01)

(58) Field of Classification Search
CPC .... A61B 6/12; A61B 6/00; A61B 6/03; A61B 6/461; A61B 6/032; A61B 6/54; A61B 6/4429; A61B 6/035; A61B 6/10; A61B 6/40; A61B 6/4208; A61B 6/44; A61B 6/462

See application file for complete search history.

(56) References Cited

U.S. PATENT DOCUMENTS 5,873,826 A 2/1999 Gono et al.
6,435,717 B1 8/2002 Kohler et al.
(Continued)

FOREIGN PATENT DOCUMENTS

DE 19943898 A1 3/2001
DE 10140740 C1 4/2003
(Continued)

*Primary Examiner* — Jurie Yun
(74) *Attorney, Agent, or Firm* — Harness, Dickey & Pierce, P.L.C.

(57) ABSTRACT

A method is for actuating a medical imaging device including a radiation source, embodied during a rotational movement around an axis of rotation to irradiate an irradiation region from a plurality of angular positions. In an embodiment, the method includes capturing an object position of a moving object relative to the irradiation region. The Method further includes actuating the medical imaging device based upon the captured object position of the moving object, such that the intensity of the radiation emitted by the radiation source for a first partial number of the plurality of angular positions in a first angular range round the axis of rotation is reduced relative to a second partial number of the plurality of angular positions in a second angular range around the axis of rotation, the captured object position being included in the first angular range.

22 Claims, 3 Drawing Sheets

(51) Int. Cl.
*A61B 6/03* (2006.01)
*A61B 6/12* (2006.01)
*A61B 6/46* (2024.01)

(56) References Cited

U.S. PATENT DOCUMENTS

| | | |
|---|---|---|
| 2003/0043956 A1 | 3/2003 | Cherek et al. |
| 2004/0017890 A1 | 1/2004 | Ruimi et al. |
| 2004/0068171 A1 | 4/2004 | Ruimi et al. |
| 2014/0072099 A1 | 3/2014 | Mukumoto et al. |
| 2014/0112438 A1 | 4/2014 | Mountney et al. |
| 2017/0215823 A1 | 8/2017 | Ivanov et al. |

FOREIGN PATENT DOCUMENTS

| | | |
|---|---|---|
| DE | 60106977 T2 | 10/2005 |
| DE | 60317411 T2 | 9/2008 |
| DE | 102014219695 A1 | 3/2016 |

METHOD FOR ACTUATING A MEDICAL IMAGING DEVICE AND MEDICAL IMAGING DEVICE

PRIORITY STATEMENT

The present application hereby claims priority under 35 U.S.C. § 119 to German patent application number DE 102020216524.6 filed Dec. 22, 2020, the entire contents of which are hereby incorporated herein by reference.

FIELD

Example embodiments of the invention generally relate to a method for actuating a medical imaging device comprising a radiation source embodied to irradiate an irradiation region from a plurality of angular positions during a rotational movement around an axis of rotation, and a related medical imaging device.

BACKGROUND

In everyday clinical practice, for medical diagnosis, medical imaging devices that comprise a radiation source, in particular an x-ray source, are mainly used. This includes, for example, the use of a computed tomography device. In a computed tomography device (CT device), for recording spatially three-dimensional image data, an x-ray source and a detector apparatus that interacts with the tomography device rotate around an axis of rotation and around an examination subject that is to be examined, for example, a patient. During the rotational movement, measured data is recorded from various projection angles, that is, from various angular positions. The measured (projection) data relates to a multiplicity of projections that contain information on the reduction in the radiation through the examination subject from the various projection angles. A two-dimensional cross-sectional image or images or a three-dimensional volume image of the examination subject can be calculated from these projections, for example, using what is known as filtered back projection or another appropriate reconstruction method, for example, an iterative reconstruction algorithm.

One intended application of a medical imaging device and also a CT device can comprise applying interventions on a patient, for example. Here, the physician carrying out the intervention and optionally further medical professionals are typically located in the examination room while radiation is emitted. As a result thereof, persons present in the examination room may be exposed to radiation. For the medical professionals present this is due primarily to scatter radiation, which is scattered on the examination subject, for example, or on parts of the medical imaging device. This radiation can vary according to the position relative to the medical imaging device or according to the position of the radiation source comprised therein relative to the medical professionals. Furthermore, in applications, in particular in applications involving an intervention, the need may arise for an at least intermittent or even continuous monitoring of the examination that is carried out on the examination subject, that is, for example, an application involving an intervention, via the image data sets captured with the medical imaging device. Therefore, in CT fluoroscopy, a CT-controlled intervention with real time image control is facilitated based upon CT image data sets. In such cases, however, direct radiation exposure can occur, for example of the hands of the physician providing the treatment, which are in or in the vicinity of the region of image data capture during the examination.

SUMMARY

Currently, when monitoring radiation exposure, the focus is frequently on the examination subject, that is, on the patient. The inventors have discovered that it is, however, just as desirable for the radiation exposure of the medical professionals to be minimized as far as possible, for example, in examinations involving an intervention, as described in the aforementioned or even in emergency examinations, in which medical professionals are also present alongside the examination subject in the direct vicinity of the medical imaging device. Here, the inventors have furtehr discovered that it is also desirable for this to be adjusted to the respective situation that currently pertains.

Embodiments of the invention provide an improved method for actuating a medical imaging device and an improved imaging device that supports a reduction of radiation exposure. Further advantageous embodiments and further developments of the invention, some of which are inventive in themselves, are set out in the claims and in the description that follows.

At least one embodiment of the invention relates to a method for actuating a medical imaging device comprising a radiation source, embodied during a rotational movement around an axis of rotation to irradiate an irradiation region from a plurality of angular positions, comprising at least the steps of capture and actuation. In the capturing step, an object position of a moving object is captured relative to the irradiation region. In the actuation step, the medical imaging device is actuated based upon the object position of the moving object that has been captured, such that the intensity of the radiation emitted by the radiation source for a first partial number of the plurality of angular positions in a first angular range around the axis of rotation is reduced relative to a second partial number of the plurality of angular positions in a second angular range around the axis of rotation, with the captured object position of the first angular range being comprised around the axis of rotation.

An embodiment of the invention further relates to a medical imaging device. The medical imaging device comprises a radiation source, which is embodied during a rotational movement around an axis of rotation to irradiate an irradiation region from a plurality of angular positions, a sensor unit, which is embodied to capture sensor data from the irradiation region, and a capture unit, which is embodied to capture an object position of a moving object relative to the irradiation region based upon the sensor data. Furthermore, the medical imaging device comprises a control unit that is embodied, based upon the captured object position of the moving object, to actuate the medical imaging device such that the intensity of the radiation emitted by the radiation source is reduced for a first partial number of the plurality of angular positions in a first angular range around the axis of rotation relative to a second partial number of the plurality of angular positions in a second angular range around the axis of rotation, the captured object position being comprised by the first angular range.

An embodiment of the invention relates to a method for actuating a medical imaging device including a radiation source, embodied during a rotational movement around an axis of rotation to irradiate an irradiation region from a plurality of angular positions, the method comprising:

capturing an object position of a moving object relative to the irradiation region; and actuating the medical imaging device based upon the object position captured, of the moving object, such that an intensity of radiation emitted by the radiation source for a first partial number of the plurality of angular positions in a first angular range around the axis of rotation is reduced relative to a second partial number of the plurality of angular positions in a second angular range around the axis of rotation, wherein the object position captured being included within the first angular range.

An embodiment of the invention relates to a medical imaging device, comprising:

a radiation source, embodied during a rotational movement around an axis of rotation, to irradiate an irradiation region from a plurality of angular positions;

a sensor unit, embodied to capture sensor data from the irradiation region;

a capture unit, embodied to capture, based upon the sensor data, an object position of a moving object relative to the irradiation region; and a control unit, embodied to actuate the medical imaging device based upon the object position captured, of the moving object, such that an intensity of radiation emitted by the radiation source for a first partial number of the plurality of angular positions in a first angular range around the axis of rotation is reduced relative to a second partial number of the plurality of angular positions in a second angular range around the axis of rotation, wherein the captured object position being within the first angular range.

BRIEF DESCRIPTION OF THE DRAWINGS

The invention is explained hereinafter via example embodiments with reference to the attached figures. The representation in the figures is schematic, highly simplified and not necessarily to scale.

DETAILED DESCRIPTION OF THE EXAMPLE EMBODIMENTS

Figure 1:
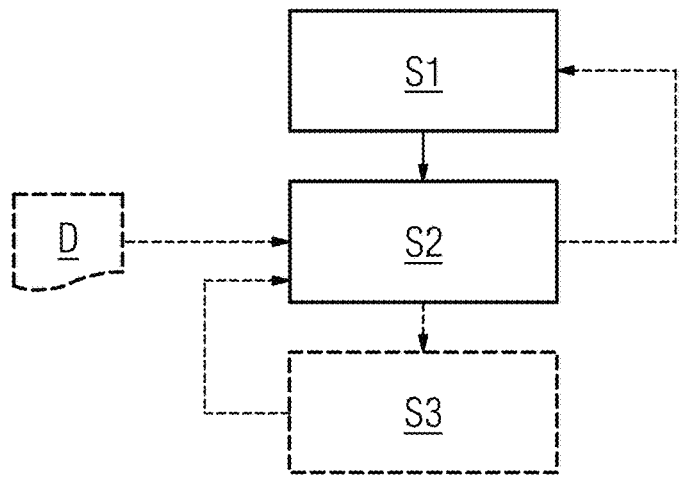
FIG. 1 shows a schematic representation of a method sequence for a method for actuating a medical imaging device.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for actuating a medical imaging device comprising a radiation source, embodied during a rotational movement around an axis of rotation to irradiate an irradiation region from a plurality of angular positions, comprising at least the steps of capture and actuation. In the capturing step, an object position of a moving object is captured relative to the irradiation region. In the actuation step, the medical imaging device is actuated based upon the object position of the moving object that has been captured, such that the intensity of the radiation emitted by the radiation source for a first partial number of the plurality of angular positions in a first angular range around the axis of rotation is reduced relative to a second partial number of the plurality of angular positions in a second angular range around the axis of rotation, with the captured object position of the first angular range being comprised around the axis of rotation.

The medical imaging device can comprise in particular an x-ray imaging device that is embodied to record an x-ray image data set based upon x-ray irradiation. Here in particular a radiation detector can be arranged opposite the radiation source, embodied based upon capturing measured data based upon the radiation emitted by the radiation source. In particular, the medical imaging device can be a CT device. However, it can also be for example, a C-arm x-ray device and/or Dyna-CT.

Here, the radiation source can essentially rotate continually around the axis of rotation and around the irradiation region. In particular, a radiation source-radiation detector combination can rotate around the axis of rotation and the irradiation region. For an imaging examination, an examination subject can be arranged inside the irradiation region, such that in the rotational movement of a radiation source-radiation detector combination in the medical imaging device, the examination subject is positioned between the radiation source and the radiation detector. During the rotational movement, the radiation source emits radiation, for example, x-ray radiation from a plurality of angular positions. The radiation detector can then detect the radiation transmitted after irradiation of the examination subject and, on the basis thereof, record a measured data set. Based upon a measured data set comprising measured data from various angular positions, an image data set can subsequently be reconstructed that essentially reflects the reduction in the radiation emitted via the object characteristics of the examination subject. The radiation source can be embodied essentially to emit radiation continually during the rotational movement around the axis of rotation at a set intensity. However, it is also possible, for example, for a pulsed emission of radiation to be provided at a set intensity.

In an example embodiment, the irradiation region comprises in particular the three-dimensional region that is impacted by a direct exposure to radiation emanating from the radiation source, that is, irradiated. This means that the irradiation region comprises in particular the three-dimensional region that is irradiated in an unscattered dispersion of the emitted radiation emanating from the radiation source during the rotational movement. The irradiation region of the medical imaging device can essentially be defined by the spatial arrangement of the radiation source and a radiation detector that is arranged opposite it in the medical imaging device and the expansion of the emitted radiation from a focus of the x-ray source in the direction of the radiation detector.

The irradiation region can additionally also comprise a region in which a greater amount of radiation emitted by the radiation source and subsequently scattered is to be expected. The radiation can, for example, be scattered on the examination subject or on parts of the medical device. In the context of the method according to the invention, the irradiation region can comprise, for example, a previously defined scattered radiation region that extends beyond the region in which direct radiation exposure is expected.

A moving object, the object position of which relative to the irradiation region is captured in the capturing step, can comprise medical professionals, or at least for example, a part of the body of a medical professional. For example, the moving object comprises at least a hand or an arm of a person who is a medical professional. The moving object can comprise medical equipment. This can apply, for example, to an intervention needle or other equipment that is used in the examination of an examination subject via the medical imaging device. A further example of medical equipment would be a part of a ventilation apparatus. In particular, the moving object can apply to an object such as is directly operated or guided during the examination of an examination subject with the aid of the medical imaging device, by part of the medical professional within, or in the spatial vicinity of, the irradiation region. Such a moving object, or the object position thereof, can then during an examination using the medical imaging device be equated with a position of the medical professional or with the position of a part of the body of the medical professional. At least, it can be used to estimate or predict a position of the medical professional. Advantageously, such a moving object can optionally be captured in a simpler and more robust manner than a moving object that is relevant to the method, for example, hands of the medical professional themself. Such a moving object can have, for instance, a constantly similar or more distinctive shape and hence be easier to capture.

For example, an intervention needle or the relevant guiding equipment and the positioning thereof can also be captured relative to the examination subject and relative to the irradiation region and in particular also in the irradiation region and can be estimated as the most probable position of a hand of the operating medical professional during an examination of the examination subject via the medical imaging device.

The capturing of the object position of the moving object can be based, for example, on sensor data from a sensor or from a plurality of sensors. The sensor data can form in particular a three-dimensional region comprising the irradiation region, such that a moving object can be captured relative to the irradiation region.

The capturing of the object position can also be facilitated by markings on the moving object itself. The capturing can also be facilitated via units and sensors on the moving object itself that can send or receive signals, for example, radio signals.

The object position of the moving object is captured relative to the irradiation region. This can comprise the object position being captured within the irradiation region. This can also comprise the object position being captured without any overlap of the object position with the irradiation region, for example, when the irradiation region is merely approached. In particular, an object position that captures the object position relative to the irradiation region such that angular information relative to the axis of rotation is assigned to the moving object can be captured. The capturing can comprise registration of the moving object relative to the irradiation region, identification of a moving object, and/or classification of a moving object as a moving object relevant to the method. The capturing of the object position relative to the irradiation region can comprise assigning an angular position or angular segment relative to the axis of rotation to the moving object.

The capturing can be carried out by a capture unit in the medical imaging device and preferably run automatically, that is, without human involvement. The capturing can also run in a partly automated manner. Alongside automatic capture, the capturing of the moving object can also comprise an action by the operating staff, for example, a moving object that has been registered can be actuated as the relevant moving object the object position of which is to be captured. The capture unit can be embodied as a data processing unit that carries out the capture automatically or partly automatically based upon the sensor data provided.

For this purpose, known methods of object recognition and/or object classification can be used. In the context of the method according to the invention, it is also conceivable for machine learning algorithms, for example an artificial neural network, to be used for the capture or for a partial aspect of the capture, for example, registering or identifying a moving object, or classifying a moving object as a moving object relevant to the method.

Actuation comprises in particular a modulation of the intensity of the radiation emitted by the radiation source during the rotational movement. Here, the intensity of the radiation emitted by the radiation source is reduced for a first partial number of the plurality of angular positions in a first angular range around the axis of rotation relative to a second partial number of the plurality of angular positions in a second angular range around the axis of rotation. Here the first angular range around the axis of rotation comprises the object position that has been captured. The first angular range can comprise in particular the angular position assigned to the moving object or an angular segment around the axis of rotation assigned to the object.

Reducing the intensity can comprise reducing the intensity to a pre-set lower value. For example, the intensity of the radiation emitted in the first angular range can be reduced to a value of less than 30%, for example, less than 10% or less than 5%, of the intensity at an angular position outside the first angular range. It can also comprise essentially no radiation being emitted.

Advantageously, during the rotational movement of the radiation source at the angular positions within the first angular range around the axis of rotation in which the moving object has been captured, less or no radiation is emitted. Advantageously, radiation exposure at the position of the moving object can be reduced.

The intensity can, for example, be modulated by actuation of the radiation source itself and hence be reduced. For example, a tube current from an x-ray source can be reduced during the rotational movement. Provision can also be made for a moveable filter or collimator made of a material that highly absorbs the radiation emitted to be used for modulating the intensity of the radiation emitted, which can be at least partly positioned in front of a beam exit window of a radiation source, and the position of which can be adjusted during the rotational movement of the radiation source.

If the medical imaging device comprises a radiation detector which is arranged opposite the radiation source and which is embodied to record measured data sets based upon the radiation emitted by the radiation source during the rotational movement at least for the second partial number of angular positions, an image data set can be reconstructed on the basis thereof. Advantageously, the second angular range comprises a sufficiently large range to reconstruct an image data set for an examination subject arranged in the irradiation region, in sufficiently high quality for the examination, based upon the second partial number of angular positions and the recorded measured data based thereon. According to a preferred variant of the method, the first angular range comprises a range not exceeding 180°, preferably not exceeding 120°.

In particular, the actuation can advantageously run automatically, that is, without human involvement or be carried out at least partly automatically based upon the object position that has been captured. Advantageously, the first angular range can be constantly, and in particular and also automatically, adjusted to the object position of the moving object such that radiation exposure in the object position, and hence for the moving object, can be reduced. Advantageously, by automatically taking into account the object position of the moving object, the method according to the invention facilitates maximum freedom of movement and action for the medical professional, without having to forgo reduced radiation exposure or without this having to be balanced against it.

According to an advantageous embodiment variant, the capturing of the object position comprises the receiving of sensor data from a sensor unit, with the capturing of the object position of the moving object being based upon the sensor data.

The sensor data can be provided via the sensor unit and received via an interface by a capture unit, embodied for determining the object position of the moving object. The capturing of the object position of the moving object can be based upon sensor data from a sensor or from a plurality of sensors. Advantageously, the use of a plurality of sensors can improve the capture. Based upon the sensor data, it is possible, for example, via an object recognition algorithm, for a moving object, at least, however, spatial position information, that is, for the object position of the moving object relative to the irradiation region to be captured. Here, it is possible to have recourse to object recognition algorithms, which are already known from the prior art.

The sensor unit or the sensor units can be arranged on the medical imaging device, for example, on a housing of the medical imaging device, or also in an equipment room in which the medical imaging device is arranged. The sensor data can advantageously depict in particular a region comprising the irradiation region, such that capturing of the object position relative to the irradiation region is facilitated in a simple manner using the sensor data. Basically, any sensors that allow spatial information to be received can be used as a sensor unit. For example, an optical sensor unit, a 2D camera or a 3D camera that allows the spatial arrangement of the moving object relative to the irradiation region to be captured visually can be used. The sensor unit could also comprise a TOF sensor unit that allows a three-dimensional representation of the surrounding surfaces in the capture range of the TOF sensor to be produced. The sensor unit can also comprise an infrared sensor, for example. Sensor data from more than one, in particular also from different types of sensor units, can be received and used for capturing the object position of the moving object. Advantageously, the combination of different sensor data can optionally improve the capturing of the object position.

Advantageously, by receiving sensor data, an effective capturing of moving objects and in particular of the object position thereof relative to the irradiation region can be facilitated.

According to a variant embodiment of the method, the object position of the moving object is captured repeatedly, and the first angular range is adjusted on the basis thereof.

Advantageously, a continual monitoring and hence actuation that is constantly adjusted to current circumstances in the medical imaging device is facilitated. Advantageously, an optimally low radiation exposure of medical professionals can be guaranteed, in particular also automatically.

According to a variant embodiment of the method, the first angular range spans a symmetrical angular range around the object position that has been captured.

Advantageously, it can be facilitated, in particular also automatically, for the moving object or a position associated therewith of the medical professional to always be in the center of a region with minimal radiation exposure. Advantageously, the radiation exposure can be minimized in a particularly effective manner.

However, it can equally well be implemented in the context of the method according to an embodiment of the invention for no symmetrical region around the captured object position to be spanned. This means that the first angular range, starting from an angular position relative to the axis of rotation and assigned to the moving object when capturing the object position, can be determined using a first partial angular range and a second partial angular range, the angular position assigned to the object being located between the first partial angular range and the second partial angular range. Here, the first partial angular range can be selected to be different from the second partial angular range. Such an implementation is useful in particular if this has been recognized as useful for reducing the radiation exposure of the medical professional, for example, using a previously drawn up room-dose chart.

Alternatively, according to a variant embodiment of the method for actuation, the first angular range can be determined, moreover, based upon a plurality of pre-set selected angular ranges, with the first angular range corresponding to the selected angular range of the plurality of pre-set selected angular ranges of which the captured object position is comprised.

For example, the selected angular ranges correspond with ranges in which it is typically highly probable that a moving object relevant to the method is present. The object position can be captured in particular relative to the selected angular ranges. The selected angular range of which the object position is comprised can then be determined as the first angular range within which the intensity of the radiation is reduced. The implementation based upon previously predetermined selected angular ranges can correspond with an advantageously simple and fast implementation.

According to a further variant embodiment of the method, the medical imaging device comprises a radiation detector, which is arranged opposite the radiation source, and which is embodied to record measured data sets based upon the radiation emitted by the radiation source during the rotational movement, at least for the second partial number of the plurality of angular positions. Based upon the measured data sets recorded, an image data set of the irradiation region is reconstructed. In the actuation step, the first angular range radiation source is then adjusted, in a subsequent rotational movement of the radiation source, based upon image information from the reconstructed image data set.

Advantageously, a position of the moving object in the irradiation region, for example, of intervention material, can be calculated from the reconstructed image data. Advantageously, this information can be used to improve the capturing of the object position or to validate a captured object position.

According to a further development, an examination subject is arranged in the region of the medical imaging device that is irradiated. In the actuation step, the first angular range is adjusted based upon information connected with the examination subject or with an examination carried out on the examination subject.

Such information can be retrievably stored, for example, on a memory unit of the medical imaging device or for the medical imaging device via an interface. For example, information connected with the examination subject or with the examination carried out on the examination subject can comprise a planned course of the examination. In particular, such information can relate to a region of the examination subject that is interacted with during an examination. For example, the information can comprise a planned needle pathway for an intervention needle during the examination.

Advantageously, this information can be used to improve the capturing of the object position or to validate a captured object position.

Furthermore, in an advantageous further development, the medical imaging device can additionally comprise a display unit. In the actuation step, in this variant of the method, the medical imaging system is actuated such that the first angular range or the second angular range is displayed via the display unit.

Advantageously, a current first or second angular range can be visualized for the medical professional and therefore a region with less radiation exposure can be characterized.

An embodiment of the invention further relates to a medical imaging device. The medical imaging device comprises a radiation source, which is embodied during a rotational movement around an axis of rotation to irradiate an irradiation region from a plurality of angular positions, a sensor unit, which is embodied to capture sensor data from the irradiation region, and a capture unit, which is embodied to capture an object position of a moving object relative to the irradiation region based upon the sensor data. Furthermore, the medical imaging device comprises a control unit that is embodied, based upon the captured object position of the moving object, to actuate the medical imaging device such that the intensity of the radiation emitted by the radiation source is reduced for a first partial number of the plurality of angular positions in a first angular range around the axis of rotation relative to a second partial number of the plurality of angular positions in a second angular range around the axis of rotation, the captured object position being comprised by the first angular range.

With regard to the medical imaging device according to an embodiment of the invention, reference is made here to the description of the method according to an embodiment of the invention. The medical imaging device according to an embodiment of the invention can be embodied in particular to carry out the methods according to an embodiment of the invention that are described in the aforementioned for actuating the medical imaging device and aspects thereof. The medical imaging device can be embodied to carry out these methods and aspects thereof, with the sensor unit, the capture unit and the control unit being embodied to carry out the corresponding method steps.

The advantages of the proposed medical imaging device essentially correspond with the advantages of the proposed method for actuating a medical imaging device. Features, advantages or alternative embodiments referred to here can equally well also be transferred to the medical imaging device and vice versa.

The medical imaging device can be embodied in particular as a computed tomography device. However, the medical device can also comprise, for example, a C-arm x-ray device and/or Dyna-CT or other x-ray imaging device that is embodied to irradiate an irradiation region from a plurality of angular positions during a rotational movement of the radiation source.

In particular, the proposed medical imaging device can additionally comprise a radiation detector opposite the radiation source, which detector is embodied to record measured data sets based upon the radiation emitted by the radiation source during the rotational movement, at least for the second partial number of the plurality of angular positions, and a reconstruction unit, embodied based upon the recorded measured data sets to reconstruct an image data set of the irradiation region. The control unit can then be embodied in particular to adjust the first angular range in a subsequent rotational movement of the radiation source, based upon image information from the reconstructed image data set.

An examination subject can be arranged in the irradiation region of the medical imaging device. In particular, the proposed medical imaging device can additionally comprise a memory unit on which information connected with the examination that has been carried out on the examination subject is retrievably stored. The control unit can be embodied to retrieve this information and adjust the first angular range on the basis thereof.

According to one embodiment variant of the medical imaging device, the device comprises a sensor unit, which comprises a sensor from the following list: optical sensor, 2D-camera, 3D-camera, infrared sensor, TOF sensor (TOF=time of flight). In particular, more than one sensor unit and a combination of different types of sensor can be comprised therein.

According to one embodiment variant of the medical imaging device, the medical imaging device comprises a display unit that can be actuated via the control unit, which display unit is embodied to display the first angular range or the second angular range.

Advantageously, a current first angular range that is not directly irradiated by the radiation source can be visualized and can guarantee direct feedback to the medical professional. Advantageously, regions less exposed to radiation and more exposed to radiation are directly discernible for the medical professional.

Various options can be provided for the display unit. For example, a display can be provided in which, for example, in an overview of the medical imaging device, the first or second angular range is visualized. Such a display used as a display unit can be arranged directly on the medical imaging device, for example, on a housing of the medical device or be incorporated in the housing. It can also be arranged separate therefrom. The first or second angular range can be color-coded via representation on such a display unit, for example. It is also possible, insofar as available, for the sensor data from a camera, which data shows the medical imaging device, to be used. In the representation, the first or second angular range, for example, can then be marked in the representation and hence visualized in a simply discernible manner for the medical professional via a colored overlay. The sensor data can already be available for use in the context of the method and also be used in a simple manner for visualization. It is equally conceivable for a first or second angular range to be visualized in an image data set captured via the medical imaging device. During an intervention, a direct display of reconstructed image data sets frequently ensues, for example, in the form of an axial cross-sectional image of the examination subject. In reconstructed image data sets, too, a first or second data set can be visualized in a simple manner for the medical professional.

According to one embodiment variant thereof, the display unit comprises one or a plurality of light sources which can be actuated for the display of the first angular range or of the second angular range via the control unit.

The light source or the light sources can serve the purpose of marking a current first or second angular range, by emitting optionally colored different light. This can comprise a range of the medical imaging device which represents the first or the second angular range, with light appropriately colored via the light source or light sources to be irradiated and hence visualize the first or second angular range on the medical imaging device. Furthermore, according to an advantageous embodiment variant, this can comprise the display unit being incorporated in a housing of the medical imaging device. For example, the display unit can comprise a plurality of light sources, for example LEDS, which are arranged in an appropriate manner in the housing of the medical imaging device, and which mark the first or second angular range by the emission of light, for example. For example, this can comprise a circular arrangement of a plurality of light sources, with in each case a region of the circular arrangement that is transferable onto the first or second angular range of the rotational movement of the light source being marked by the emission of light. The marking can comprise differently colored light, for example.

Advantageously, an easily comprehensible visualization can be achieved in an advantageously simple manner with a display unit via light sources. Integration in a or on a housing can advantageously facilitate the transmission of the first or second angular range onto the actual spatial range on the medical imaging device and make an additional representation avoidable by having separate display systems.

According to one embodiment variant, the housing comprises a tunnel-shaped aperture, through which the axis of rotation runs. The display unit can then be arranged in particular radially around the tunnel-shaped aperture and the axis of rotation. The display unit can then provide, in the form of a plurality of light sources for example, a direct and easily comprehensible visualization of the current first or second angular range around the axis of rotation, in a particularly advantageous manner.

Furthermore, provision can be made, in the context of a further development and minimization of radiation exposure for medical professionals, for a current or accumulated radiation exposure of the medical professionals to be displayed directly on the medical imaging device or in the examination room. For example, a dose display can be provided on the medical imaging device or in the examination room. In addition, an acoustic signal to alert the user to too high a level of radiation exposure would be conceivable. Here, high radiation exposure can be defined by a threshold value that has been set in advance. Advantageously, improved monitoring and reduction of the radiation exposure of medical professionals can be facilitated by continual feedback.

In order to calculate the radiation exposure or radiation dose of the medical professionals in the examination room, provision can be made, for example, for the position-dependent radiation exposure during installation of the medical imaging device to be captured initially in advance in the examination room. Such a determination carried out in advance can also serve the purpose of defining a scatter radiation region, already described in the aforementioned, as part of an irradiation region that is considered in the method according to the invention. What is known as a room-dose chart can be drawn up. This room-dose chart can either be drawn up by measuring the dose with an appropriate scattering body at given reference positions in the examination room or can also be calculated with the aid of dose simulations based upon the known properties of the device, of the patient, and of the room. A combination of the two methods could also be conceivable here, that is, an initial reference simulation for the dose distribution in the vicinity of the medical imaging device, which simulation is then adjusted to the local circumstances and calibrated or validated with the aid of intermittent dose measurements in the examination room.

Via a sensor unit, for example, a 2D or 3D camera or other appropriate sensor unit that is arranged in the examination room and is embodied to capture or map the examination room, the position of the medical professional present in the examination room can be captured and radiation exposure can be estimated via the room-dose chart. The estimated radiation exposure can then be displayed. For example, the radiation exposure can be expressed as a dose output per hour. Such a calculation and/or display of the radiation exposure of medical professionals in an examination room can readily be carried out without the aforementioned display or capture of a first or second angular range as per the method according to the invention for actuating the medical imaging device.

Furthermore, it would be conceivable to visualize the position-dependent radiation exposure in the examination room. The radiation exposure may vary considerably according to the position in the examination room. For example, the position-dependent radiation exposure in the examination room can be displayed via an appropriate display unit. For example, based upon sensor data from a sensor unit, for example, a 2D or 3D camera or other appropriate sensor unit, a representation of the examination room can be displayed on a display, with regions of the room with different levels of radiation exposure being marked. For example, a region with the lowest radiation level or a region with the highest radiation level can be marked. The marking can for instance be equivalent to a color marking. It would be equally conceivable to irradiate and hence to visualize regions of the room with different levels of radiation exposure in an appropriate manner via light sources, for example, in different colors. It would also be conceivable to visualize regions of the room with different levels of radiation exposure via light sources incorporated in the room, in particular in the floor. In this way, a region in the room with the lowest level of radiation can be marked in a simple, easily recognizable manner. A position-dependent radiation exposure in an examination room can be calculated or estimated, for example, in a similar manner to that described in the aforementioned using a room-dose chart. Such a display could also be implemented independent of a display or capture described in the aforementioned of a first or second angular range as per the method according to the invention for actuating the medical imaging device.

In the context of embodiments of the invention, features described with reference to different embodiments of the invention and/or to different categories of claim (method, use, apparatus, system, arrangement, etc.) can be combined to form further embodiments of the invention. For example, a claim that relates to an apparatus can also be further developed with features that are described or for which protection is sought in connection with a method, and vice versa. Functional features of a method can be implemented using substantive components that have been embodied accordingly. Alongside the embodiments explicitly described in this application, it is possible to conceive of diverse further embodiments of the invention, at which a person skilled in the art may arrive without going beyond the scope of the invention as specified in the claims.

The use of the indefinite article "a" or "an" does not preclude the relevant feature from also being present in plurality. The use of the term "comprise" does not preclude the possibility of terms connected with the term "comprise" from being identical. For example, the medical imaging apparatus comprises the medical imaging apparatus. The term "unit" does not preclude the subject to which the term "unit" refers from consisting of a plurality of components that can be spatially separated from one another.

The term "based upon" can be understood in the context of the present application in particular in the sense of the term "using". In particular, a wording according to which a first feature is generated (or alternatively determined, captured etc.) based upon a second feature does not preclude the first feature from being generated (or alternatively determined, captured etc.) based upon a third feature.

FIG. 1 shows a schematic method sequence for a method for actuating a medical imaging device.

The medical imaging device that is actuated via the method comprises in particular a radiation source 9, embodied during a rotational movement around an axis of rotation 5 to irradiate an irradiation region 6 from a plurality of angular positions.

Step S1 of the method comprises the capturing S1 of an object position of a moving object 4 relative to the irradiation region 6. Here the irradiation region 6 comprises at least the three-dimensional region that is impacted, that is, irradiated, by direct radiation exposure emanating from the radiation source 9 of the medical imaging device. The irradiation region can also comprise a scatter radiation region. The capturing S1 can comprise registration of the moving object 4 relative to the irradiation region, identification of a moving object 4, and/or classification of a moving object 4 as a moving object 4 relevant to the method. The capturing of the object position relative to the irradiation region 6 can comprise in particular assigning an angular position or angular segment relative to the axis of rotation 5 to the moving object 4. The moving object 4 can comprise a medical professional person, for example, a physician administering treatment, or at least, for example, a part of their body. For example, the moving object 4 comprises at least a hand or an arm of a medical professional person. The moving object 4 can alternatively or additionally also comprise medical equipment, for example an intervention needle.

The capturing S1 preferably runs automatically or at least partly automatically via a capture unit CU of the medical imaging device.

Step S2 comprises the actuation S2 of the medical imaging device based upon the captured object position of the moving object 4, such that the intensity of the radiation emitted by the radiation source 9 is reduced for a first partial number of the plurality of angular positions in a first angular range α around the axis of rotation 5 relative to a second partial number of the plurality of angular positions in a second angular range around the axis of rotation 5, wherein the captured object position is comprised of the first angular range α. The second angular range can then in particular comprise the region of the rotational movement that is not comprised by the first angular range α.

A reduction in the intensity can comprise in particular reducing the intensity to a pre-set, lower value, for example, less than 10% or less than 5%, of the intensity at an angular position outside the first angular range α. It can also comprise there being essentially no radiation emitted within the first angular range α.

Preferably the actuation will run automatically, that is, without human involvement, or be carried out at least partly automatically based upon the captured object position using a control unit CR of the medical imaging device.

The capturing S1 of the object position can comprise receiving sensor data from a sensor unit SU, with the capturing of the object position of the moving object 4 being based on the sensor data. The sensor unit SU or the sensor units SU can be arranged on the medical imaging device, for example on a housing 3 of the medical imaging device, or also in an equipment room in which the medical imaging device is arranged. The sensor data advantageously shows in particular a region comprising the irradiation region 6, such that the capturing of the object position relative to the irradiation region 6 is facilitated via the sensor data. Any sensors that allow spatial information to be received can basically be used as a sensor unit, for example, an optical sensor unit, a 2D camera or a 3D camera, an infrared sensor or a TOF sensor.

The object position of the moving object 4 can preferably be captured repeatedly and the first angular range α can be adjusted on the basis thereof in order to guarantee continuous monitoring.

The method can additionally optionally comprise the step S3, wherein an image data set of the irradiation region 6 is reconstructed based upon recorded measured data sets. In the actuation step S2, the first angular range α can be adjusted during a subsequent rotational movement of the radiation source 9 based upon image information from the reconstructed image data set. Alternatively or additionally, the method can comprise the first angular range α being adjusted during the actuation step S2, based upon information D connected with the examination subject 1 or with an examination carried out on the examination subject 1. The information D connected therewith can be a planned needle pathway of an intervention needle during the examination, for example.

Furthermore, the medical imaging device can additionally comprise a display unit 41, wherein in the actuation step S2 the medical imaging system is additionally actuated such as to display the first angular range α or the second angular range via the display unit 41.

Figure 2:
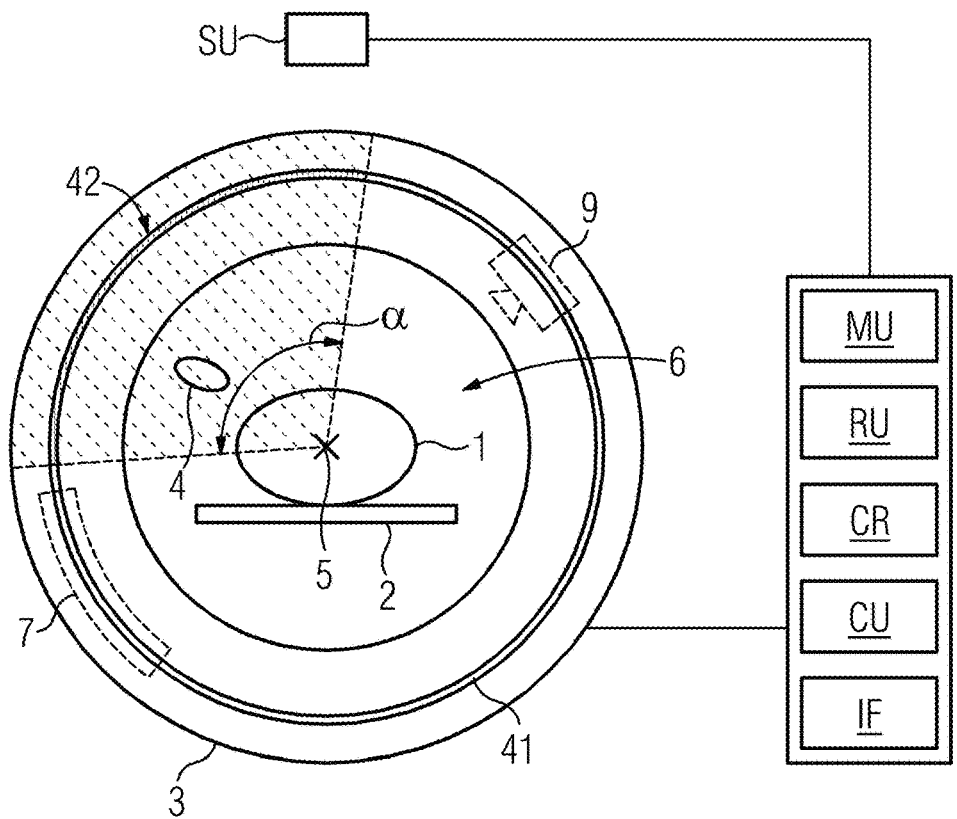
FIG. 2 shows a schematic representation of a medical imaging device in an example embodiment.

FIG. 2 shows a schematic representation of a medical imaging device that can be actuated via a method as described in connection with FIG. 1. In the variant shown, the medical imaging device is embodied in particular as a CT device.

The medical imaging device comprises a radiation source 9, embodied during a rotational movement around an axis of rotation 5 to irradiate an irradiation region 6 from a plurality of angular positions.

The medical imaging device additionally comprises a radiation detector 7 opposite the radiation source 9, which detector is embodied to record measured data sets at least for the second partial number of the plurality of angular positions based upon the radiation emitted by the radiation source 9 during the rotational movement.

The medical imaging device additionally comprises a housing 3 in which the radiation source 9 and the radiation detector are arranged. The radiation source 9 and the radiation detector 7 are rotatably mounted inside the housing 3 around the irradiation region 6 and around the axis of rotation 5. Inside the irradiation region 6, a patient is supported as an examination subject 1 on a patient support apparatus 2. The mode of functioning of a CT device and the capturing of image data sets based upon measured data sets captured via the radiation detector 7 is widely known to those skilled in the art. In particular, an image data set of the examination subject 1, which data set essentially reflects the reduction in the radiation emitted by virtue of the object characteristics of the examination subject 1, can be reconstructed based upon a measured data set comprising measured data from various angular positions during the rotational movement of the radiation source 9 and of the radiation detector 7.

The medical imaging device additionally comprises a sensor unit SU, embodied to capture sensor data from the irradiation region 6. The sensor unit SU can comprise in particular a sensor from the following list: camera, optical sensor, 3D-camera, infrared sensor, TOF sensor (TOF=time of flight). In this case, the sensor unit SU is drawn separately from the housing 3 of the medical imaging device. However, it is also possible for the sensor unit SU to be arranged on the housing 3. Likewise it is possible for a plurality of, and also in particular also for different types of, sensor units SU to be used.

The medical imaging device further comprises a capture unit CU, embodied to capture an object position of a moving object 4 relative to the irradiation region 6 based upon the sensor data, and a control unit CR, embodied to actuate the medical imaging device based upon the captured object position of the moving object 4, such that the intensity of the radiation emitted by the radiation source 9 for a first partial number of the plurality of angular positions in a first angular range α around the axis of rotation 5 is reduced relative to a second partial number of the plurality of angular positions in the second angular range around the axis of rotation 5, with the captured object position being comprised of the first angular range α.

A moving object 4, the object position of which is captured in the capturing step S1 relative to the irradiation region 6, can, as already described in FIG. 1 in connection with the method, comprise medical professionals, or at least a part of a body of a medical professional, for example, a hand. The moving object 4 can also comprise medical equipment. This can relate for example, to an intervention needle or to other equipment that is used during an examination of an examination subject 1. In particular, the moving object 4 can relate to such an object that is directly operated or guided, during the examination of an examination subject 1 using the medical imaging device, by a part of the medical professional within or in the spatial vicinity of the irradiation region.

The medical imaging device additionally comprises a reconstruction unit RU, embodied to reconstruct an image data set of the irradiation region 6 based upon the recorded measured data sets. The control unit CR can then be embodied in particular to adjust the first angular range α during a subsequent rotational movement of the radiation source 9, based upon image information from the reconstructed image data set.

A patient is arranged as an examination subject 1 in the irradiation region 6 of the medical imaging device. In particular, in the embodiment variant shown, the proposed medical imaging device additionally comprises a memory unit MU, on which information connected with an examination carried out with the examination subject 1 or with the examination subject 1 can be retrievably stored. The control unit CR can then be embodied to retrieve this information and to adjust the first angular range α on this basis.

The medical imaging device in the embodiment variant shown additionally comprises a display unit 41 which can be actuated via the control unit CR and which is embodied to display the first angular range α or the second angular range. The display unit 41 can comprise one or a plurality of light sources, which can be actuated to display the first angular range α or the second angular range via the control unit CR. In the embodiment variant shown, the display unit 41 is incorporated in a housing 3 of the medical imaging device. In particular, the display unit 41 is arranged radially around the tunnel-shaped aperture through which the axis of rotation 5 runs and around the axis of rotation 5. In the variant shown, the display unit 41 is embodied in the form of an LED strip, which is actuated to visualize the range 42 that corresponds with the current first angular range α, and mark it in a manner that is clearly visible for the medical professional via the emission of light. Alternatively or also additionally, display units that are embodied in a different way, for example, in the form of a display arranged on the imaging device or in the equipment room, can also be used.

The control unit CR and/or reconstruction unit RU and/or capture unit CU can be in particular a computer, a microcontroller or an integrated circuit. A control unit CR and/or reconstruction unit RU and/or capture unit CU can have hardware elements or software elements, for example, a microprocessor or what is known as an FPGA or "Field Programmable Gate Array". A control unit CR and/or reconstruction unit RU and/or capture unit CU can be combined in a computing unit, wherein the computing unit can comprise a plurality of sub-processing units that carry out the various steps of the respective methods.

A memory unit MU can be implemented as a non-permanent working memory, such as a Random-Access Memory, RAM for short, or as a permanent mass memory, such as a hard disk, USB stick, SD card or solid-state disk.

The medical imaging device can additionally comprise one or a plurality of interfaces IF, which facilitate communication between units of the medical imaging device. For example, the sensor data in the sensor unit SU can be retrieved via an interface IF. An interface IF can be a hardware or software interface, for example, a PCI bus, a USB or a Firewire.

The medical imaging device can additionally comprise an output apparatus, not shown here, for example, a display, which facilitates representation of a reconstructed image data set. Furthermore, it can comprise an input apparatus. The input apparatus and the output apparatus can facilitate, for example, an interaction with the medical imaging device, a confirmation or a triggering of a method step by a user.

Figure 3:
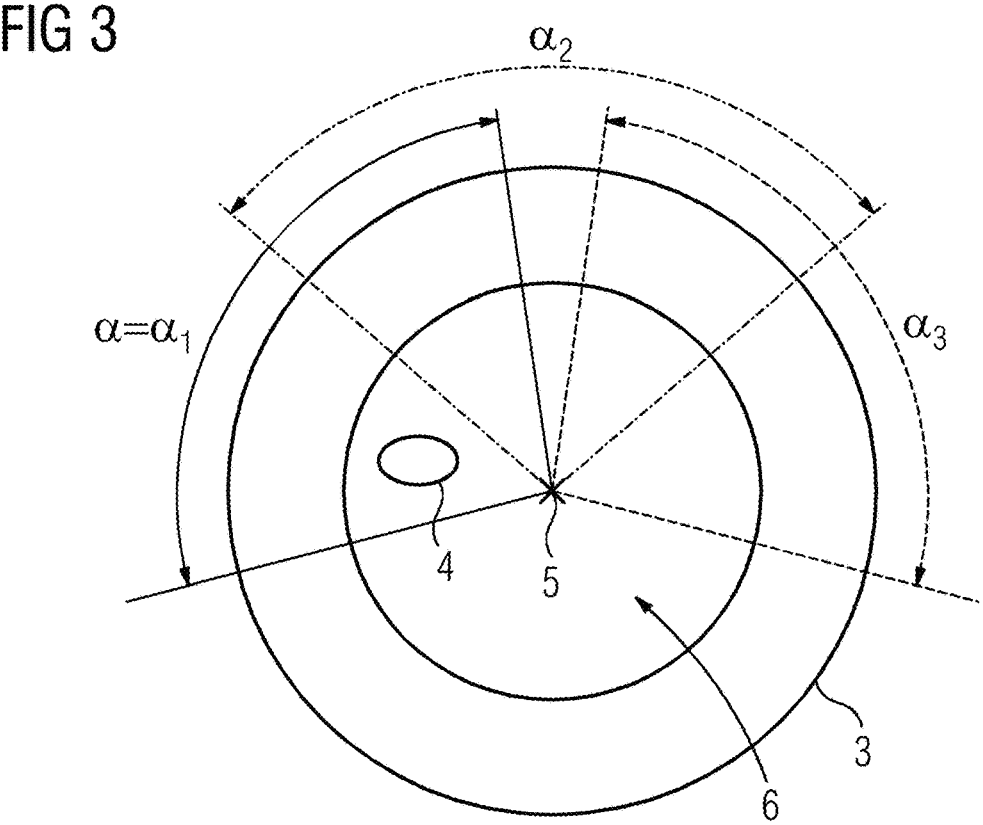
FIG. 3 shows an illustration of a first angular range for the actuation of the medical imaging device according to a first embodiment variant.

FIG. 3 shows an illustration of a first angular range $\alpha$ for the actuation of the medical imaging device according to a method described in the aforementioned as per one variant of the method. Here, for the actuation S2, the first angular range $\alpha$ is captured based upon a plurality of predetermined selected angular ranges $\alpha 1$, $\alpha 2$, $\alpha 3$, wherein the first angular range $\alpha$ corresponds with the selected angular range $\alpha 1$, $\alpha 2$, $\alpha 3$ from the plurality of predetermined selected angular ranges $\alpha 1$, $\alpha 2$, $\alpha 3$, of which the captured object position of the moving object 4 is comprised. For example, the selected angular ranges correspond with ranges in which there is typically a high probability that a moving object relevant to the method is present.

Figure 4:
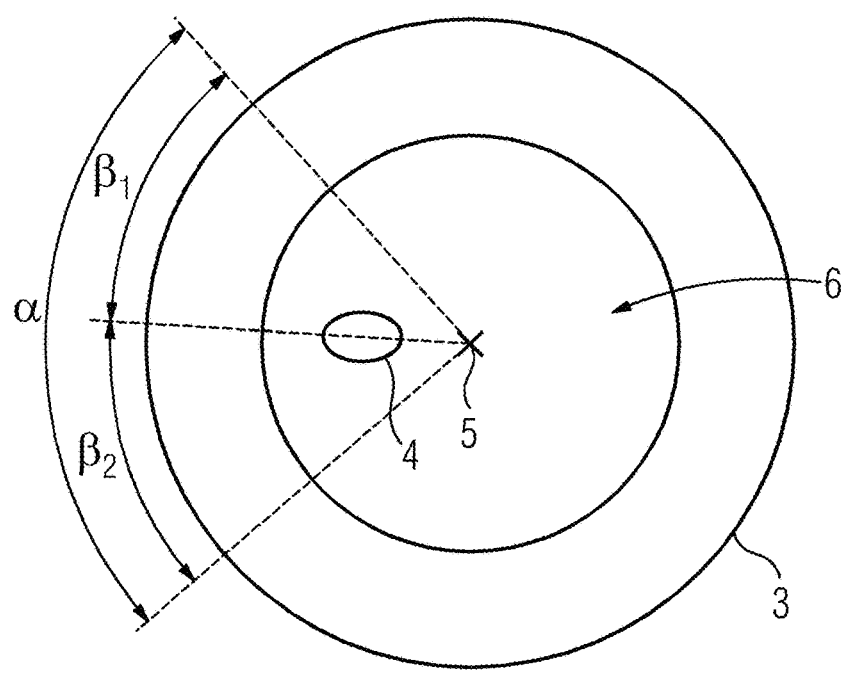
FIG. 4 shows an illustration of a first angular range for the actuation of the medical imaging device according to a second embodiment variant.

FIG. 4 shows an illustration of a first angular range $\alpha$ for the actuation of the medical imaging device as per a method described in the aforementioned according to a further embodiment variant. Here the first angular range $\alpha$ spans a symmetrical angular range around the captured object position of the moving object 4. This means that, starting from an angular position assigned to the moving object, partial angular ranges $\beta 1$ and $\beta 2$, equal in size, are spanned, which together form the first angular range $\alpha$, and wherein the angular position assigned to the object is located between the partial angular ranges $\beta 1$ and $\beta 2$. A symmetrical design can represent an advantageously simple implementation.

However, in a further development, it is also conceivable for no symmetrical range around the captured object position to be spanned. This means that the first angular range $\alpha$ can be determined, starting from an angular position relative to the axis of rotation 5 and assigned to the moving object 4 in the capturing S1 of the object position, by a first partial angular range $\beta 1$ and a second partial angular range $\beta 2$, wherein the angular position assigned to the object is located between the first partial angular range $\beta 1$ and the second partial angular range $\beta 2$. Here the partial angular ranges $\beta 1$ and $\beta 2$, which together form the first angular range $\alpha$, can be selected not to be equal in size but of different sizes. Such an implementation is particularly useful when this has been acknowledged as useful for reducing the radiation exposure of the medical professional during an examination, for example, via a previously created room-dose chart.

Irrespective of the embodiment variant, the first angular range $\alpha$ preferably comprises a range of 180° maximum, even more preferably 120° maximum.

Figure 5:
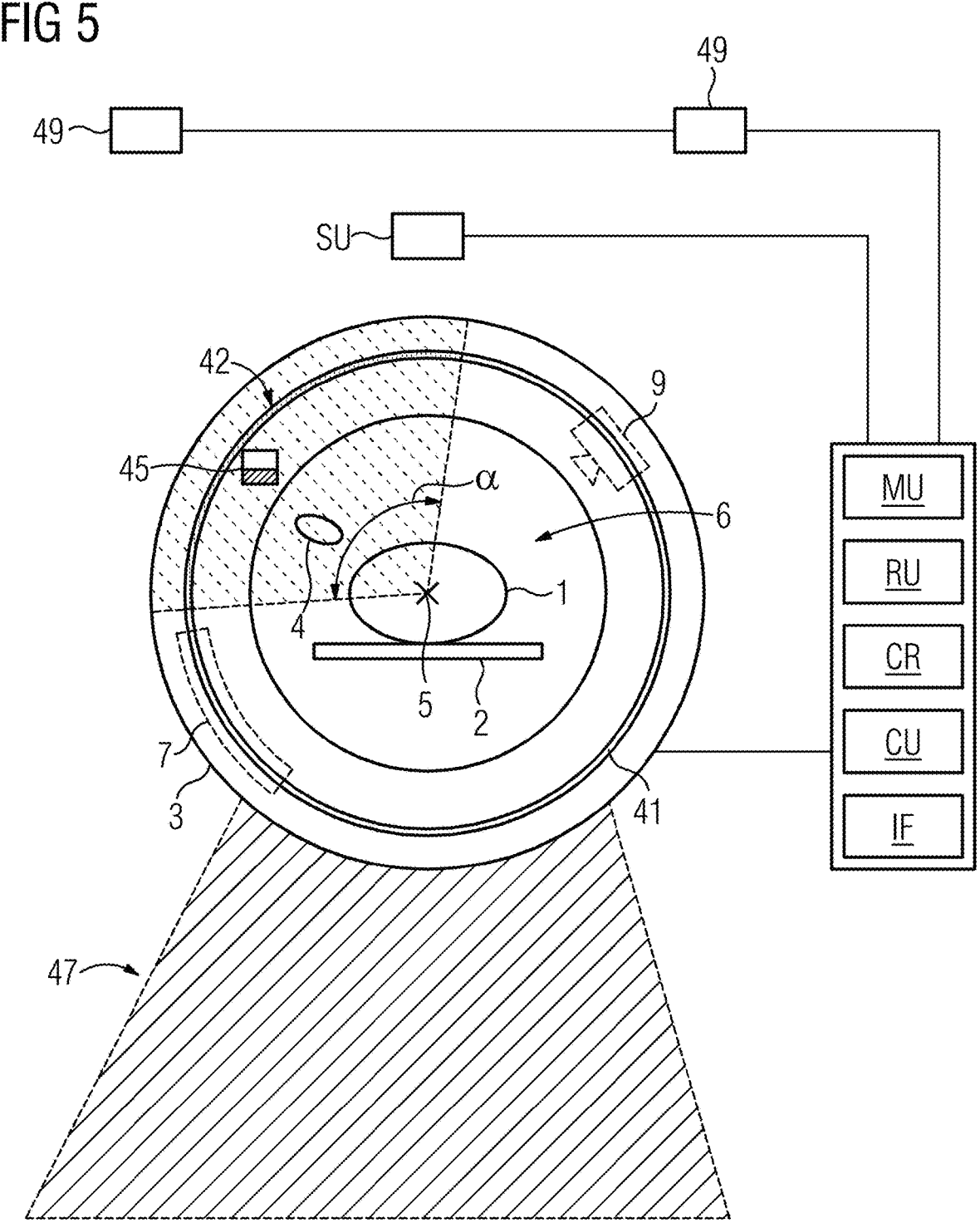
FIG. 5 shows a schematic representation of a medical imaging device according to a further example embodiment variant.

FIG. 5 shows a schematic representation of a medical imaging device in an example embodiment according to a further embodiment variant.

The embodiment variant comprises essentially all the features of the medical imaging device shown in FIG. 2. Corresponding elements are denoted by the same reference characters. In this variant, the medical imaging device additionally comprises a further display unit 45. The display unit serves as a dose display for a current or cumulative radiation exposure for medical professionals. In this variant, the dose display 45 is provided in the form of a display on the housing 3 of the medical imaging device.

Furthermore, further sensor units 49 are provided, for example, in the form of a camera or other appropriate sensor unit, which is arranged in the examination room and is embodied to capture or map the examination room. The position of the medical professional present in the examination room can be captured via the sensor units 49 and a position-dependent radiation exposure can be estimated, for example, via a room-dose chart that has been drawn up in advance. The estimated radiation exposure can be continually adjusted via the dose display 45. In the embodiment shown, the dose display is arranged on the housing 3. In other embodiments this display can also be arranged separately from the housing 3.

It would be further conceivable to display the radiation exposure in the examination room in a position-dependent manner. For example, a region with the lowest radiation and a region with the highest radiation 47 can be marked in the examination region by an appropriate display system. An appropriate display system can comprise a representation of the equipment room on the display, with regions of the room with different exposure levels being marked. It would be equally conceivable to irradiate regions of the room with different exposure levels using light sources in an appropriate manner, for example, with different colors, or to visualize regions of the room with different exposure levels via light sources in the equipment room, in particular incorporated in the floor, by emitting light.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for actuating a medical imaging device including a radiation source, embodied during a rotational movement around an axis of rotation to irradiate an irradiation region from a plurality of angular positions, the method comprising:
   capturing an object position of a moving object relative to the irradiation region;
   actuating the medical imaging device based upon the object position captured, of the moving object, such that an intensity of radiation emitted by the radiation source for a first partial number of the plurality of angular positions in a first angular range around the axis of rotation is reduced relative to a second partial number of the plurality of angular positions in a second angular range around the axis of rotation, wherein the object position captured is included within the first angular range; and
   displaying, on a display unit, at least one of the first angular range or the second angular range, the display unit being arranged radially around a tunnel-shaped aperture of the medical imaging device and including a plurality of light sources in a circular arrangement.

2. The method of claim 1, wherein the capturing of the object position includes receiving sensor data from a sensor unit and wherein the object position of the moving object is captured during the capturing, based upon the sensor data received.

3. The method of claim 2, wherein the object position of the moving object is captured repeatedly during the capturing, and the first angular range is adjusted based upon repeated capturing.

4. The method of claim 2, wherein the first angular range spans a symmetrical angular range around the object position captured.

5. The method of claim 2, wherein for the actuating, the first angular range is determined based upon a plurality of selected angular ranges, and wherein the first angular range corresponds with a selected angular range of the plurality of selected angular ranges, the captured object position being included within the selected angular range.

6. The method of claim 2, wherein the first angular range comprises at least one range of 180° maximum.

7. The method of claim 2, wherein, during the capturing of the object position, an angular position relative to the axis of rotation is assigned to the moving object, and for the actuating, the first angular range is determined starting from the angular position of the moving object, using a first partial angular range and a second partial angular range, wherein the angular position assigned to the moving object is located between the first partial angular range and the second partial angular range.

8. The method of claim 2, wherein a radiation detector is arranged opposite the radiation source, the radiation detector being embodied to record measured data sets based upon the radiation emitted by the radiation source during the rotational movement at least for the second partial number of the plurality of angular positions, the method further comprising:
   reconstructing an image data set of the irradiation region based upon the recorded measured data sets; and
   adjusting the first angular range, during a subsequent rotational movement of the radiation source, based upon image information from the image data set reconstructed.

9. The method of claim 8, wherein an examination subject is arranged in the irradiation region of the medical imaging device, and wherein, during the adjusting, the first angular range is adjusted based upon information connected with the examination subject or with an examination carried out on the examination subject.

10. The method of claim 9, wherein the information is a planned needle pathway of an intervention needle during the examination.

11. The method of claim 1, wherein the object position of the moving object is captured repeatedly during the capturing, and the first angular range is adjusted based upon repeated capturing.

12. The method of claim 1, wherein, during the capturing of the object position, an angular position relative to the axis of rotation is assigned to the moving object, and for the actuating, the first angular range is determined starting from the angular position of the moving object, using a first partial angular range and a second partial angular range, wherein the angular position assigned to the moving object is located between the first partial angular range and the second partial angular range.

13. The method of claim 1, wherein the first angular range spans a symmetrical angular range around the object position captured.

14. The method of claim 1, wherein for the actuating, the first angular range is determined based upon a plurality of selected angular ranges, and wherein the first angular range corresponds with a selected angular range of the plurality of selected angular ranges, the captured object position being included within the selected angular range.

15. The method of claim 1, wherein the first angular range comprises at least one range of 180° maximum.

16. The method of claim 1, wherein a radiation detector is arranged opposite the radiation source, the radiation detector being embodied to record measured data sets based upon the radiation emitted by the radiation source during the rotational movement at least for the second partial number of the plurality of angular positions, the method further comprising:
   reconstructing an image data set of the irradiation region based upon the recorded measured data sets; and adjusting the first angular range, during a subsequent rotational movement of the radiation source, based upon image information from the image data set reconstructed.

17. The method of claim 16, wherein an examination subject is arranged in the irradiation region of the medical imaging device, and wherein, during the adjusting, the first angular range is adjusted based upon information connected with the examination subject or with an examination carried out on the examination subject.

18. The method of claim 17, wherein the information is a planned needle pathway of an intervention needle during the examination.

19. The method of claim 1, further comprising:
displaying on a dose display unit an indication of at least one of current or cumulative radiation exposure for a medical professional.

20. The method of claim 1, further comprising:
displaying on a dose display unit a room dose chart indicating radiation exposure throughout an examination room including the medical imaging device.

21. A medical imaging device, comprising:
a radiation source configured, during a rotational movement around an axis of rotation, to irradiate an irradiation region from a plurality of angular positions;
a sensor unit configured to capture sensor data from the irradiation region;
a capture unit configured to capture, based upon the sensor data, an object position of a moving object relative to the irradiation region;
a control unit configured to actuate the medical imaging device based upon the object position captured, of the moving object, such that an intensity of radiation emitted by the radiation source for a first partial number of the plurality of angular positions in a first angular range around the axis of rotation is reduced relative to a second partial number of the plurality of angular positions in a second angular range around the axis of rotation, wherein the captured object position is within the first angular range; and
a display unit configured to display the first angular range or the second angular range, the display unit being arranged radially around a tunnel-shaped aperture of the medical imaging device, being actuatable via the control unit, and including a plurality of light sources in a circular arrangement.

22. The medical imaging device of claim 21, wherein the display unit is incorporated in a housing of the medical imaging device, the housing including the tunnel-shaped aperture through which an axis of rotation runs.

* * * * *